US010765854B2

(12) United States Patent
Law et al.

(10) Patent No.: US 10,765,854 B2
(45) Date of Patent: Sep. 8, 2020

(54) PORT CONNECTOR FOR MEDICAL WASTE FLUID RECEPTACLES AND METHODS OF USE

(71) Applicant: Allegiance Corporation, Waukegan, IL (US)

(72) Inventors: Kok Hern Law, Singapore (SG); Rajesh Gladwin Dharmadas, Singapore (SG); Wei Chen Lie, Singapore (SG)

(73) Assignee: ALLEGIANCE CORPORATION, Chicago, IL (US)

(*) Notice: Subject to any disclaimer, the term of this patent is extended or adjusted under 35 U.S.C. 154(b) by 461 days.

(21) Appl. No.: 15/688,787

(22) Filed: Aug. 28, 2017

(65) Prior Publication Data

US 2018/0056056 A1 Mar. 1, 2018

Related U.S. Application Data

(60) Provisional application No. 62/381,010, filed on Aug. 29, 2016.

(51) Int. Cl.
*A61M 39/00* (2006.01)
*A61M 39/10* (2006.01)
(Continued)

(52) U.S. Cl.
CPC ............ *A61M 39/10* (2013.01); *A61J 1/1475* (2013.01); *A61M 1/0001* (2013.01);
(Continued)

(58) Field of Classification Search
CPC .. A61M 1/0001; A61M 1/0086; A61M 39/10; A61M 39/221; A61M 2039/1077;
(Continued)

(56) References Cited

U.S. PATENT DOCUMENTS 893,469 A 7/1908 Frieda
1,366,789 A 1/1921 Graham
(Continued)

FOREIGN PATENT DOCUMENTS

CN 201379898 Y 1/2010
EP 0659090 A1 6/1995
(Continued)

OTHER PUBLICATIONS

International Search Report and Written Opinion for Application No. PCT/US2017/48877, dated Mar. 8, 2018, 11 pages.

*Primary Examiner* — Benjamin J Klein
(74) *Attorney, Agent, or Firm* — Arent Fox LLP

(57) ABSTRACT

Aspects of the present disclosure include a connector that is suitable for connecting medical suction tubing with at least two different types of fluid ports of a medical fluid collection system. In certain aspects, the connector includes a generally cylindrical body portion having a cylindrical outer surface extending generally parallel to a central longitudinal axis of the body portion, and an inner surface defining a primary conduit extending through the connector. At least one lateral closure wall extends radially outward from the outer surface of the body portion. At least one annular skirt wall extends longitudinally from the at least one lateral closure wall, including a first annular skirt wall that serves to receive an open mouth of a first fluid port having a relatively small diameter, and a second annular skirt wall that serves to receive an open mouth of a second fluid port having a relatively larger diameter.

14 Claims, 7 Drawing Sheets

100 112 323 150 322 150a 300 130 100 102 110 142 332 142a 330 335 108 130

(51) Int. Cl.
*A61J 1/14* (2006.01)
*A61M 1/00* (2006.01)
*A61M 39/22* (2006.01)

(52) U.S. Cl.
CPC ... *A61M 39/221* (2013.01); *A61M 2039/1077* (2013.01); *A61M 2039/1094* (2013.01)

(58) Field of Classification Search
CPC ............ A61M 2039/1094; A61J 1/1475; A61J 1/1487
See application file for complete search history.

(56) References Cited

U.S. PATENT DOCUMENTS

| | | | |
|---|---|---|---|
| 3,019,932 | A | 2/1962 | Singiser |
| 3,807,457 | A | 4/1974 | Logsdon |
| 3,850,341 | A | 11/1974 | Bart |
| 4,384,580 | A | 5/1983 | Leviton |
| 4,388,922 | A | 6/1983 | Telang |
| 4,577,771 | A | 3/1986 | Martinez |
| 4,969,565 | A | 11/1990 | Justal et al. |
| 5,071,413 | A | 12/1991 | Utterberg |
| 5,267,983 | A | 12/1993 | Oilschlager et al. |
| 5,458,586 | A | 10/1995 | Adiletta |
| 5,470,324 | A | 11/1995 | Cook et al. |
| 5,569,222 | A | 10/1996 | Haselhorst et al. |
| 5,624,417 | A | 4/1997 | Cook et al. |
| 5,725,516 | A | 3/1998 | Cook et al. |
| 5,848,994 | A | 12/1998 | Richmond |
| 5,954,957 | A | 9/1999 | Chin-Loy et al. |
| 6,086,574 | A | 7/2000 | Carroll et al. |
| 6,213,996 | B1 | 4/2001 | Jepson et al. |
| 6,409,220 | B1 | 6/2002 | Wing et al. |
| 6,652,495 | B1 | 11/2003 | Walker |
| 6,808,515 | B2 | 10/2004 | Takahashi et al. |
| 6,875,204 | B1 | 4/2005 | Hopkins et al. |
| 6,910,720 | B2 | 6/2005 | Shimei et al. |
| 7,481,243 | B2 | 1/2009 | Michaels et al. |
| 8,231,525 | B2 | 7/2012 | Cohen et al. |
| D681,201 | S | 4/2013 | Mcfarland et al. |
| 8,506,549 | B2 | 8/2013 | Breuer-Thal et al. |
| 8,834,407 | B2 | 9/2014 | Greeson, Jr. et al. |
| 9,080,436 | B2 | 7/2015 | Tetzlaff et al. |
| D748,775 | S | 2/2016 | Greeson, Jr. et al. |
| D749,717 | S | 2/2016 | Kobida et al. |
| D775,723 | S | 1/2017 | Rowe et al. |
| D782,665 | S | 3/2017 | Mintz et al. |
| 2010/0022986 | A1* | 1/2010 | Breuer-Thal .......... A61M 5/162 604/414 |
| 2015/0320638 | A1 | 11/2015 | Becker et al. |
| 2015/0343121 | A1 | 12/2015 | Kobida et al. |

FOREIGN PATENT DOCUMENTS

| | | | |
|---|---|---|---|
| EP | 0711538 | A1 | 5/1996 |
| WO | 2015034045 | A1 | 3/2015 |
| WO | 2016035788 | A1 | 3/2016 |

* cited by examiner

PORT CONNECTOR FOR MEDICAL WASTE FLUID RECEPTACLES AND METHODS OF USE

CROSS-REFERENCE TO RELATED APPLICATIONS

This application claims priority to, and the benefit of, U.S. Provisional Patent Application Ser. No. 62/381,010, filed Aug. 29, 2016, the entirety of which is incorporated herein by reference.

BACKGROUND

Field of the Invention

Port connector systems and methods as disclosed herein may be related to the field of medical fluid collection, disposal and other related methods, and more specifically, certain aspects may relate to medical waste fluid collection and/or disposal systems that utilize a rigid or semi-rigid canister for directly or indirectly storing various fluids and liquid waste; such canisters may include a flexible, semi-rigid or rigid liner for isolating fluid from the canister walls. These canisters and liners may include a rigid or semi-rigid lid provided with one or more openings or ports for communicating vacuum and/or waste fluid into and out of the interior of the canisters or liners.

Background of the Technology

The medical environment, which could include operating rooms, emergency rooms, patient rooms and other healthcare facilities, generates liquid waste. Liquid waste may include secretions removed from a patient's body, which may include blood and other bodily fluids, irrigation liquids, or other fluids, such as suspended solids and various other particles. A typical waste canister of the related art is a storage container in which negative pressure (also interchangeably referred to herein as "suction" or "vacuum") is communicated so as to thereby create negative pressure inside the canister to draw or drain fluids and liquid waste from at or near a drainage or surgical site. Vapors, smoke, and particles and small solids suspended in liquids or gasses are also commonly drawn in the suction canister. Gasses containing solids are typically filtered and evacuated from the canister, while other fluids and liquid waste are collected in the canister. Canister systems may include a flexible, semi-rigid or rigid liner to isolate fluids and liquid waste from the canister walls. Flexible liners are liners are frequently secured to the lid in an expanded or compacted state and are expanded to fit inside the canister walls when a seal is formed between the lid and the canister. Collected waste fluid, including gasses, may enter through a port in the lid or canister, typically referred to as an inlet port or a patient port. A suction source may be communicated with the interior of the canister via a second port in the lid or canister, typically referred to as a vacuum port. Gasses collected in the canister may be drawn by suction through a filter that may be positioned in the vacuum path between the collected fluid and the suction source. Canisters or lids may have additional ports such as a tandem port for connecting additional canisters in a tandem configuration and a larger port for removing samples of collected fluid or adding solidifier or for evacuating the contents of the canister for disposal. Fluid ports of the type used in suction canister systems typically include a cylindrical spout surrounding a particular opening in the lid and extending upward from an upper surface of the lid. An interior surface of the spout defines a conduit extending through the port, the conduit communicating the interior of the canister or liner with the exterior thereof. After use, the canister or the flexible or semi-flexible liner may be sealed, for example by capping or plugging the spouts of the various ports, and disposed of in a desired manner. In a system that isolates fluid and liquid waste from the outer walls of the canister, the canister may be reused with multiple new lid and/or liner assemblies. The canisters may be removed and discarded or sanitized periodically.

The abovementioned fluid collection systems and methods may include multiple canisters connected in a tandem configuration via one or more fluid conduits, such as medical suction tubing, to increase fluid and liquid waste capacity. Canisters connected in tandem may be connected to a suction source in parallel such that each canister has an independent connection to the suction source. Alternatively, the canisters may be connected to the suction source in series such that an end canister is connected directly to the suction source and suction is communicated from the suction source into the interior of the end canister, and to an upstream canister via a tandem connection that communicates the interior of the end canister with the interior of the upstream canister. Multiple upstream canisters may be connected in this manner, and a first canister, being farthest upstream, may have a suction tube to collect fluids from a source and to deposit the fluids in the first canister. When the collected fluid fills the first canister, fluid in the first canister passes into a second canister via a tandem tube connected between a tandem port of the first canister and an inlet port of the second canister.

The vacuum port of each canister may include a shut-off valve upstream of the vacuum port to prevent fluids and other debris from entering and contaminating the vacuum system. Initially, shut-off valves were typically mechanical in design such as a "floating ball" system that will close the vacuum port when liquid levels reach the height of the valve. Presently, canister systems typically employ a porous plastic filter/valve that may be treated with a moisture-reactive powder, such as polysaccharide, polyacrylate or certain proteins, which serves to block the filter upon contact with aqueous liquid or aerosols, thus preventing potential contamination of equipment or spaces downstream of the filter. Such moisture-reactive agents are dormant until the filter/valve is contacted by aqueous liquid or aerosol. As soon as the liquid starts to penetrate into the filter/valve, the liquid causes the powder to swell and form a colloidal gel. This cohesive gel structure serves to shut off the flow of fluids through the valve and into the vacuum system.

In situations where one or more canisters become filled, fluid may reflux or come out of one or more ports under certain circumstances. For example, if vacuum is removed from the system, the pressure differential between atmosphere on the one hand and the cavity between the canister and the lining one the other, created by the vacuum between the canister and the liner, is removed. Removal of the vacuum allows the liner to collapse somewhat, due to liner elasticity, increasing the internal pressure on the fluid inside the liner. This increased pressure could cause fluid to be pushed out through the suction tube toward the patient or otherwise out of the canister, which may lead to contamination of personnel and other hazards.

When multiple canisters are connected in tandem, a significant number of tubes may be necessary for connecting the multiple canisters to the vacuum system, the fluid source, and to each other. Moreover, several different suction canister systems are sold by various manufacturers. These canister systems typically vary with respect to the type quantity, location, and size of ports, and each may require different types of port connectors to properly connect tubing to the various types of ports. The use of, attachment, and removal of numerous tubes and connectors may be visually unappealing, distracting, and hazardous. Furthermore, the large variety of tubing and connector configurations can make system setup and removal complicated, confusing, and can increase the likelihood of errors. It is therefore desirable to reduce the quantity of different variations of tubes and connectors that are inventoried and used at medical facilities.

SUMMARY

Certain aspects of the present disclosure may include a connector that is suitable for connecting medical suction tubing with at least two different types of fluid ports in a medical fluid collection system. In certain aspects, the connector includes a generally cylindrical main body portion having an upper portion, a middle portion, and a lower portion. The main body portion includes a cylindrical outer surface extending generally parallel to a central longitudinal axis of the body portion, and an inner surface defining a primary conduit extending through the connector. At least one lateral closure wall extends radially outward from the main body portion. At least one annular skirt wall extends longitudinally from the at least one lateral closure wall, including a first annular skirt wall that serves to receive an open mouth of a first fluid port having a relatively small diameter, e.g., a diameter of about 15 mm, and a second annular skirt wall that serves to receive an open mouth of a second fluid port having a relatively larger diameter, e.g., a diameter of about 25 mm.

In certain aspects, an inner surface of the first annular skirt wall may be configured to engage an outer surface of a spout (also herein interchangeably referred as a port cone or port riser) of a first port in an interference fit such that the connector may be secured to the first port. Similarly, an inner surface of the second annular skirt wall may be configured to engage an outer surface of a spout of a second port. Alternatively, an outer surface of the second annular skirt wall may be configured to engage an inner surface of the spout of the second port. In various other aspects, an outer surface of the first annular skirt wall may be configured to engage an inner surface of the spout of the first port. It will be appreciated that the connector may be configured with any number of annular skirt walls, each of which may be configured to engage either an inner surface or an outer surface of a particular port's spout. In various other aspects, the connector may be configured such that one or more annular skirt walls are configured to engage an outer surface of a spout of a first port and an inner surface of a spout of a second port, the spout of the second port having a larger diameter than the spout of the first port. In certain other aspects, one or more annular skirt wall may include either internal or external, or both internal and external threads, barbs, rings, embossments, or any other similar gripping, coupling, sealing or locking feature.

In certain aspects, the upper portion of the connector may include a generally cylindrical or conical riser portion for receiving a tube or similar device capable of communicating fluid and/or suction to and from the conduit of the connector. The riser portion may include barbs, ribs, tabs, or other features for improving connection strength between the riser portion and various connected accessories. In certain aspects, the lower body portion may extend downward a greater distance than the skirt walls of the connector, thereby defining a lower mouth (i.e., opening) of the primary conduit that is positioned lower than the annular skirt walls. In various aspects, the lower body portion may include a shoulder, step, ledge, ribs, tabs or other similar feature for gripping or engaging a port to provide secure or locking engagement of the connector with the port. In certain aspects, an outer portion of the connector includes spaced apart radial protrusions, gnarled surfaces, or other similar features to provide a better gripping area for a user to aid in installation and removal of the connector.

Any feature, structure, or step disclosed herein can be replaced with or combined with any other feature, structure, or step disclosed herein, or omitted. Further, for purposes of summarizing the disclosure, certain aspects, advantages, and features of the systems, devices, and methods have been described herein. It is to be understood that not necessarily any or all such advantages are achieved in accordance with any particular embodiments disclosed herein. No individual aspects of this disclosure are essential or indispensable.

BRIEF DESCRIPTION OF THE FIGURES

Embodiments of the present disclosure are described by way of the following drawings pointing out various details of the systems, devices and methods of the present disclosure. The main features and advantages of the present disclosure will be better understood with the following descriptions, claims, and drawings, where:

Figure 1:
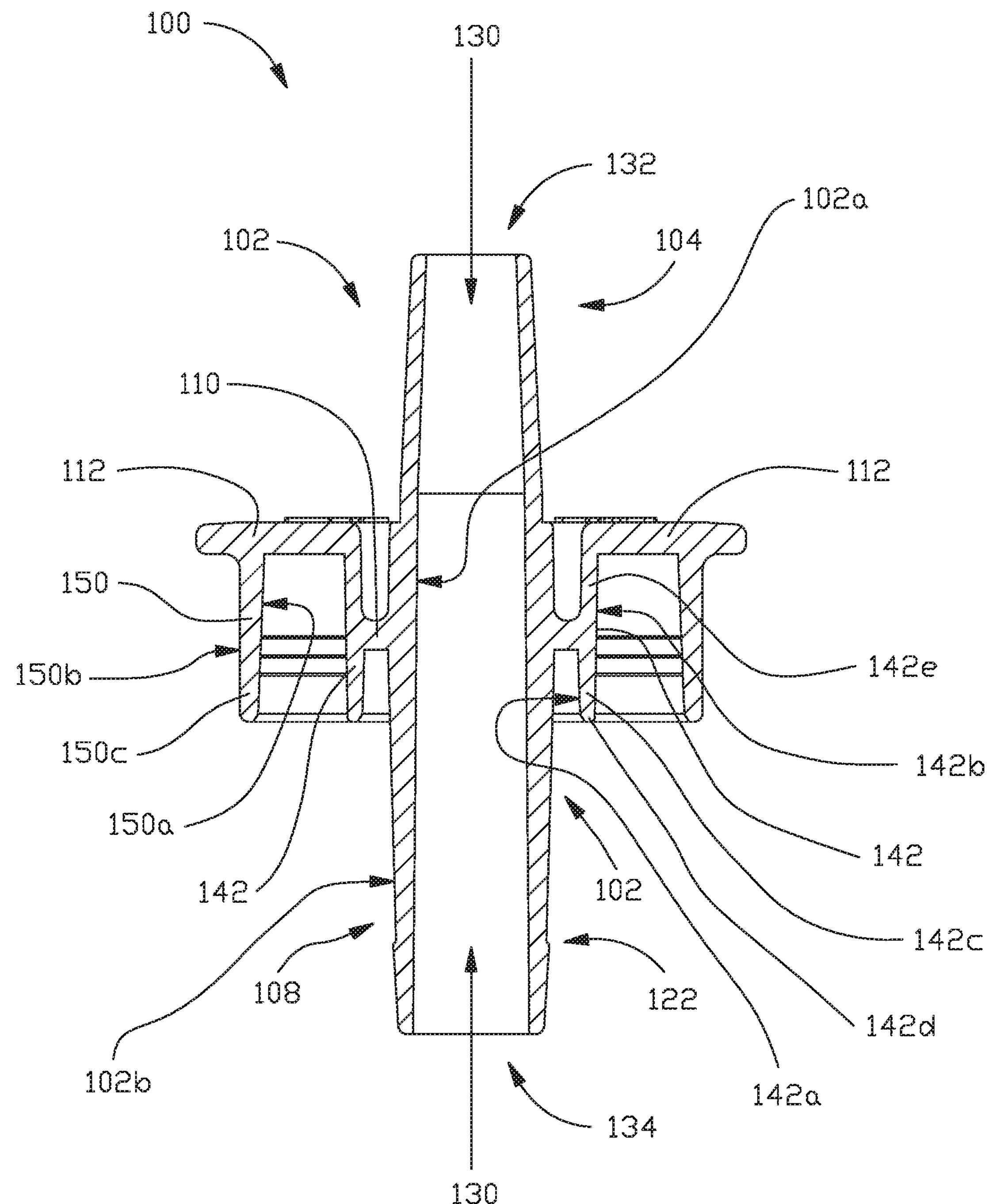
FIG. 1 is a section view of a connector in accordance with certain aspects of the present disclosure.

It should be understood that the figures are diagrammatic and schematic representations of exemplary embodiments of the systems and methods of the present disclosure, and are neither limiting nor necessarily drawn to scale.

DETAILED DESCRIPTION

The detailed description set forth below, in connection with the appended drawings, is intended as a description of various configurations and is not intended to represent the only configurations in which the concepts described herein may be practiced. The detailed description includes specific details for the purpose of providing a thorough understanding of the various concepts. However, it will be apparent to those skilled in the art that these concepts may be practiced without these specific details.

Various aspects of the systems and devices disclosed herein may be illustrated by describing components that are connected, coupled, attached, bonded and/or joined together. As used herein, the terms "connected", "coupled", "attached", "bonded" and/or "joined" are used interchangeably to indicate either a direct connection between two components or, where appropriate, an indirect connection to one another through intervening or intermediate components. Additionally, unless otherwise specified, these terms are used interchangeably to indicate a connection in which one or more degrees of freedom are not rigidly constrained between two components (e.g., a pivoting connection, a translating connection, a pivoting and translating connection, an elastic connection, a flexible connection, etc.), or a rigid or substantially rigid connection in which all degrees of freedom are constrained or substantially constrained between the two components.

Relative terms such as "lower" or "bottom", "upper" or "top", and "vertical" or "horizontal" may be used herein to describe one element's relationship to another element illustrated in the drawings. It will be understood that relative terms are intended to encompass different orientations of the systems and devices in addition to the orientation depicted in the drawings. By way of example, if aspects of a connector as shown in the drawings are turned over, elements described as being on the "bottom" side of the other element would then be oriented on the "top" side of the other elements as shown in the relevant drawing. The term "bottom" can therefore encompass both an orientation of "bottom" and "top" depending on the particular orientation of the drawing.

Reference will now be made to figures wherein like structures are provided with like reference designations. It should be understood that the figures are diagrammatic and schematic representations of exemplary embodiments of the systems and methods of the present disclosure, and are neither limiting nor necessarily drawn to scale.

One exemplary embodiment of a connector in accordance with aspects of the present disclosure is illustrated in FIG. 1. In this embodiment, the connector 100 includes a generally cylindrical main body portion 102 having an upper portion 104, a middle portion 106, and a lower portion 108. The main body portion 102 has a generally cylindrical outer surface 102*b* extending along a central longitudinal axis of the main body portion, and an inner surface 102*a* that defines a primary conduit 130 extending through the connector from an upper opening 132 at the upper portion 104 of the main body 102 to a lower opening 134 at the lower portion 108. An inner lateral closure wall 110 extends radially outward from the outer surface 102*b* of the body portion 102 and couples the main body with an inner annular skirt wall 142. The inner skirt wall 142 has an inner surface 142*a* and an outer surface 142*b*, and a lower portion 142*c* extends downward from the inner closure wall 110 to a lower rim 142*d*. An upper portion 142*e* of the inner skirt wall 142 extends upward from the inner closure wall 110 and terminates at an outer lateral closure wall 112. The outer closure wall 112 extends radially outward from the inner skirt wall 142. The outer skirt wall 150 extends longitudinally downward from the outer lateral closure wall 112 to a lower rim 150*c* and has an inner surface 150*a* and an outer surface 150*b*. In various alternative embodiments, the inner closure wall couples the inner skirt wall with a first portion of the main body and the outer closure wall may couple the outer skirt wall with a second, different portion of the main body.

Figures 2A, 2B, 2C:
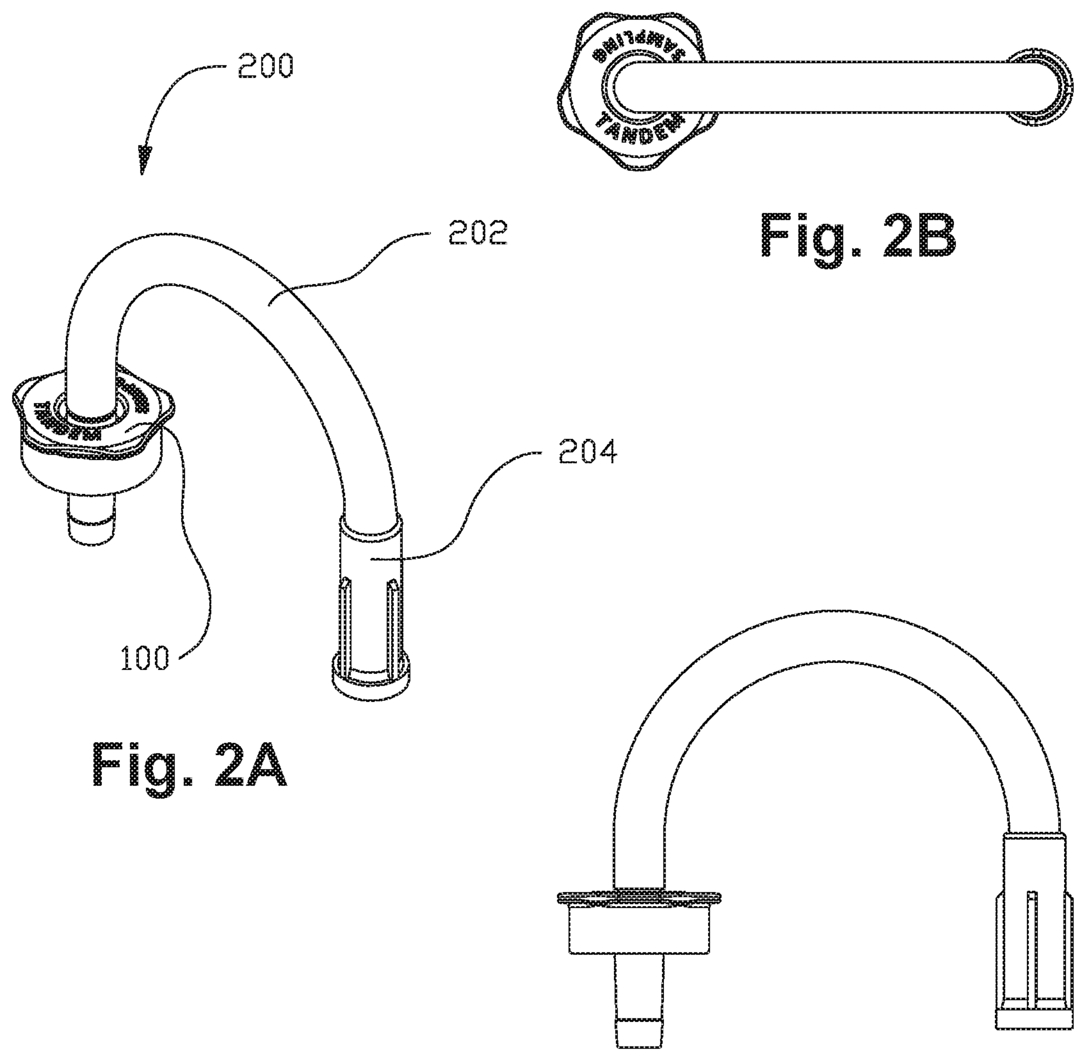
FIGS. 2A-2C are perspective, top, and side views of a tandem tube assembly including a connector in accordance with certain aspects of the present disclosure.

The upper portion 104 of the main body 102 may be configured to mate with a tube or similar device capable of communicating fluid and/or suction to and from the primary conduit 130 of the connector 100. For example, as illustrated in FIGS. 2A-2C, a tandem tube assembly 200 may include a connector 100, a segment of medical suction tubing 202 connected, for example by sliding an open end of the tube segment over the upper portion 104 of the main body 102, and optionally a second connector connected to the other end of the tube segment 202, for example the fitting 204 commonly used to connect tubing to a typical patient port of a fluid collection system. Alternatively, the second connector may be another connector in accordance with the present disclosure, such as connector 100.

Figure 3:
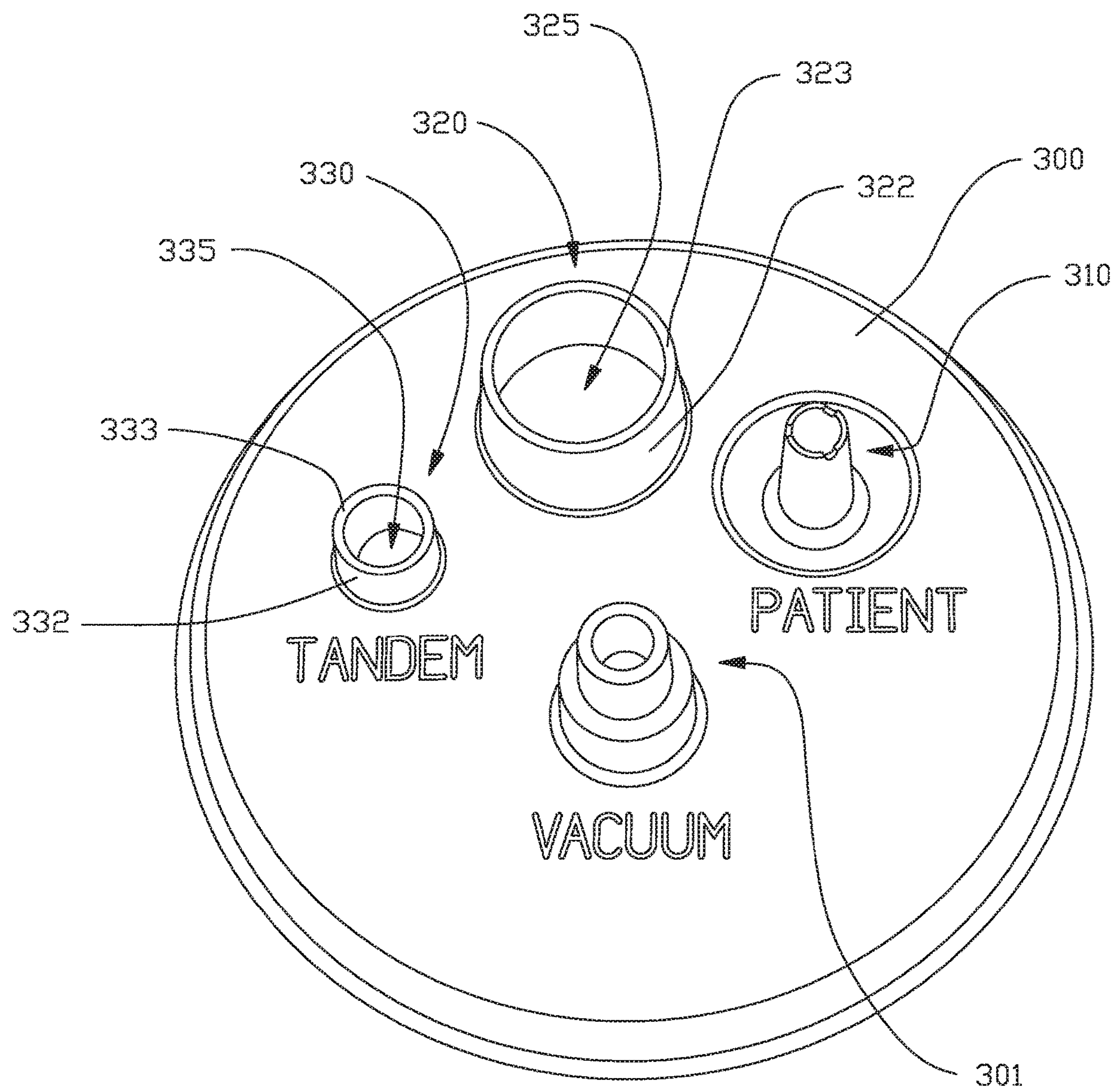
FIG. 3 is a perspective view of a common fluid collection canister system lid.
Figure 4:
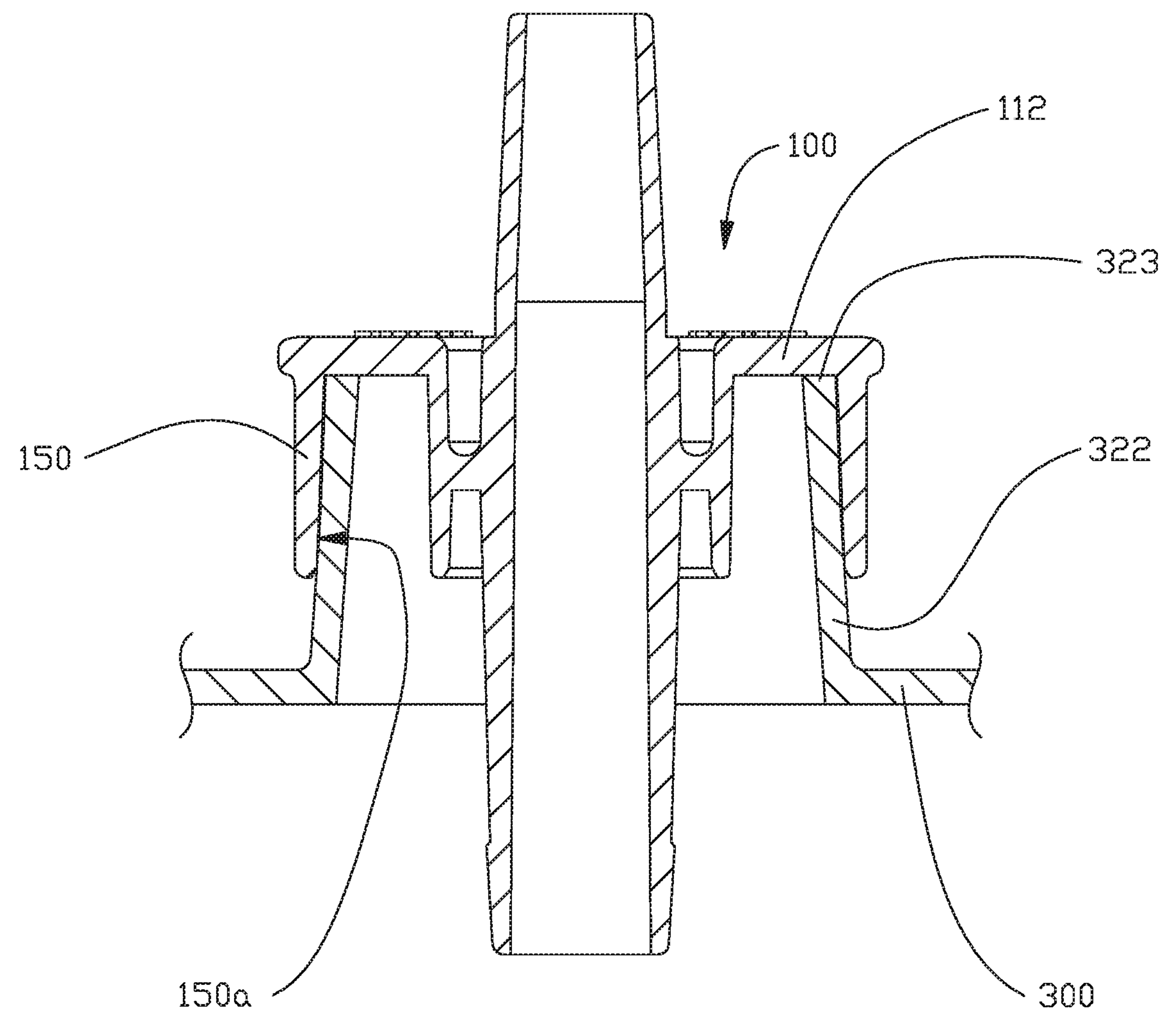
FIG. 4 is a detail section view illustration of a sampling port of the lid of FIG. 3.

The connector 100 is configured to connect with at least two different fluid collection system ports. For example, as illustrated in FIG. 3, one example fluid collection canister system lid 300 useable with the connector 100 is configured to close an open end of a medical waste fluid container such as a rigid suction canister. The lid 300 has a vacuum port 301 for supplying suction to the canister, a patient port 310 that serves as a waste fluid inlet, a sampling port 320 that has a relatively larger diameter opening than the patient port 310, and a tandem port 330 that may be used to connect various accessories or a tandem tube connection with another canister for connecting multiple canister systems in series. Each port typically has a port cone or port riser that is generally cylindrical or conical in shape and extends upward from an upper surface of the lid to a rim. For example, as shown in FIG. 4, a sampling port 320 includes a port riser 322 extending upward from an upper surface of lid 300 to a rim 323. The port riser 322 defines a port lumen 325 extending from an upper port opening 326 to an opening in the lid 300. Some ports, for example the tandem port 330 illustrated in FIG. 5, also include a lower port cone 338 that extends downward from a lower surface of the lid 300 to a lower rim 339. As such, the tandem port lumen 335 extends from an opening at the rim 333 of the tandem port riser 332 through the opening in the lid 300 to the opening at the lower rim 339 of the lower port cone 338.

Figure 5:
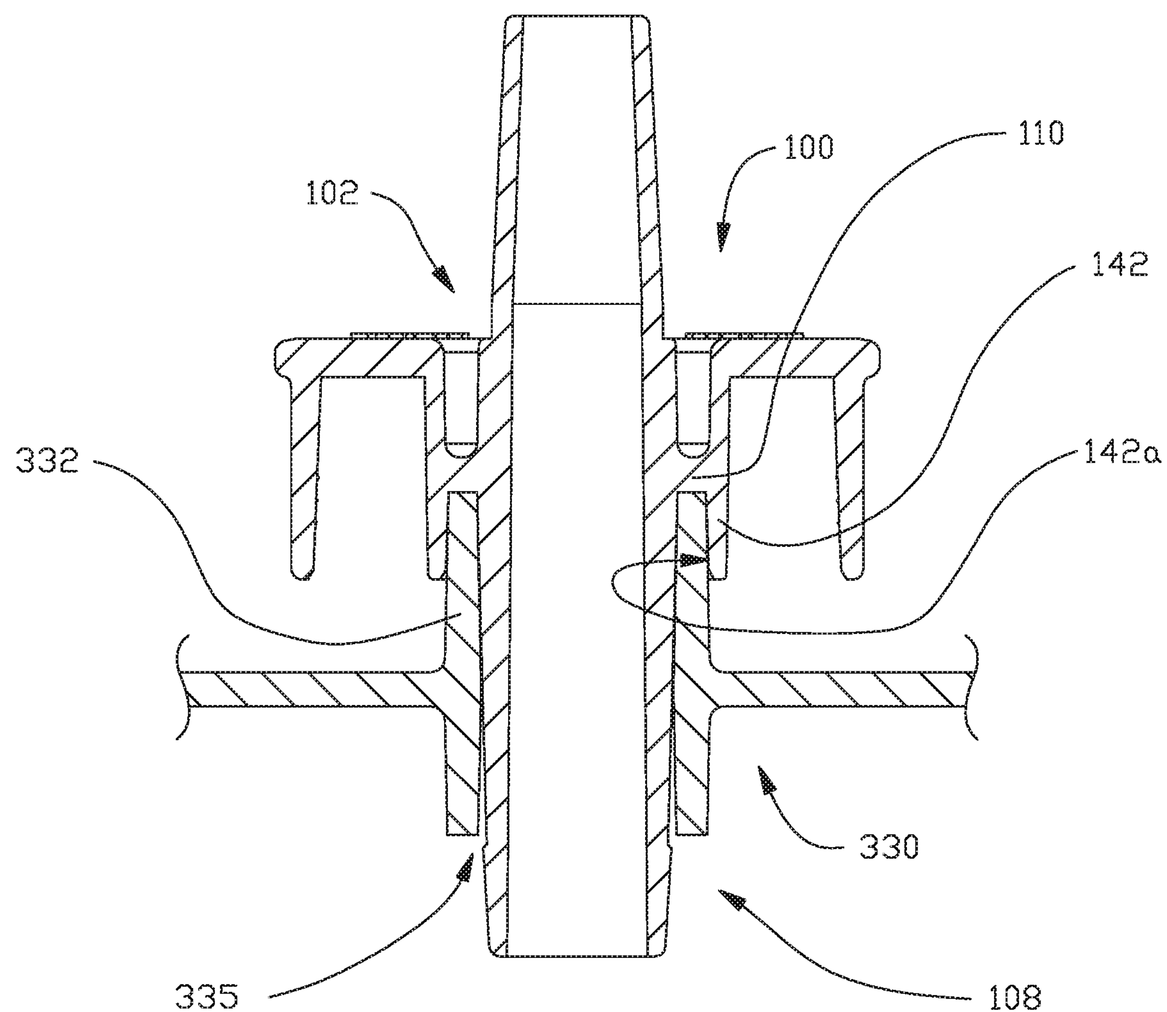
FIG. 5 is a detail section view illustration of a tandem port of the lid of FIG. 3.

The connector 100 of the embodiment of FIG. 1 is configured such that when the connector 100 is mated with the sampling port 320 as shown in FIG. 4, the inner surface 150*a* of the outer skirt wall 150 engages an outer surface of the sampling port riser 322. Additionally, when the connector 100 and the sampling port 320 are fully mated, the rim 323 of the sampling port riser 322 abuts the lower surface of the outer closure wall 112, which functions as a stop to position the connector 100 at a desired height relative to the lid 300. The connector 100 is also configured to mate alternatively with a tandem port 330 as shown in FIG. 5 such that the inner surface 142*a* of the inner skirt wall 142 engages an outer surface of the tandem port riser 332, and the rim 333 of the tandem port riser 332 abuts the lower surface of the inner closure wall 110. Additionally, the lower portion 108 of the main body 102 extends through the lumen 335 of the tandem port riser 332 to below the lower rim 339 of the lower port cone 338. A ledge 122 provided at the outer surface of the lower portion 108 of the main body 102 may have an outer diameter slightly larger than an inner diameter of the port lumen 335 to provide an interference fit to provide tactile and/or audible indication of a positive engagement of the connector 100 with the tandem port 330 and/or to increase the amount of pulling force required to remove the connector 100 from the tandem port 330.

Figure 6:
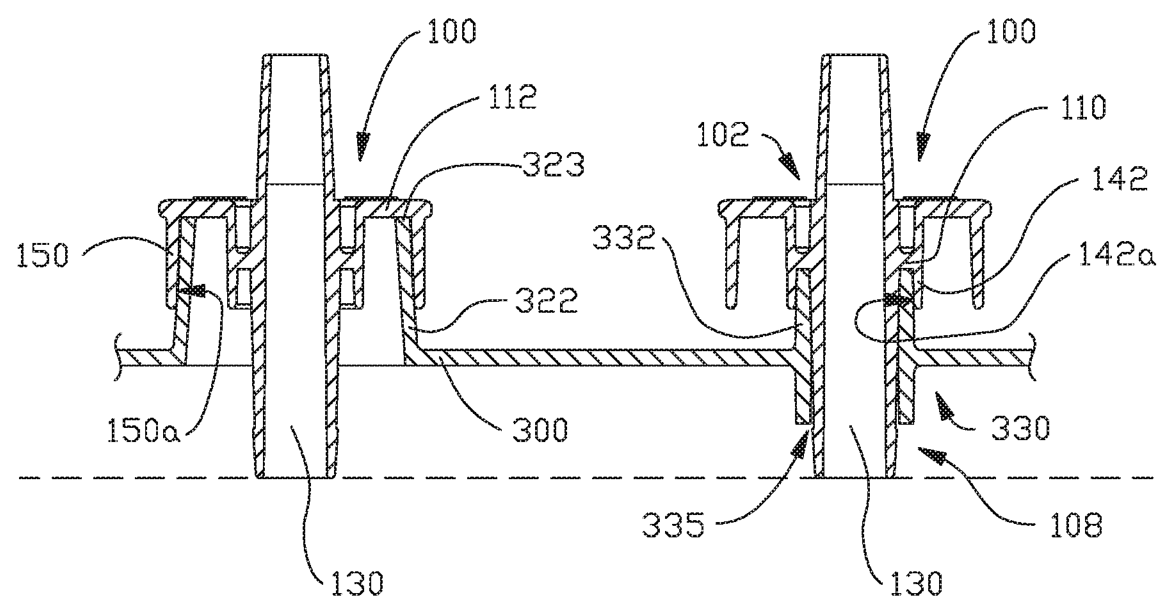
FIG. 6 is a detail section view of the connector of FIG. 1 connected to the sampling port and the tandem port of the lid of FIG. 3.

As illustrated in FIG. 6, the connector 100 is configured such that regardless of whether the connector is mated with the sampling port 320 or the tandem port 330, the lower opening 134 of the primary conduit 130 is maintained at substantially the same vertical height relative to the lid 300. In medical waste fluid collection systems, if the level of fluid collected in a canister is too high, there is an increased risk of fluid reflux, splashing, spillage, and leakage. When the connector 100 is used to connect two canisters in tandem, suction supplied via the second canister will draw excess fluid into the primary conduit 130 once the level of fluid collected in the first canister rises to the height of the lower opening 134. Thus, the amount of fluid collected in a canister may be controlled by varying the length of the lower portion 108 of the main body 102. The differing heights of the inner and outer closure walls 110, 112 ensures that the height of the lower opening 134 of the connector 130—and therefore the maximum height of fluid collected in the canister—is the same regardless of whether the connector 100 is connected to the sampling port 120 or the tandem port 130. In various aspects, one or more stops such as a shoulder, step, rib, indent, or other similar feature may be provided to cooperate with a port riser to control the height of the connector when it is fully mated with a port.

Figure 7:
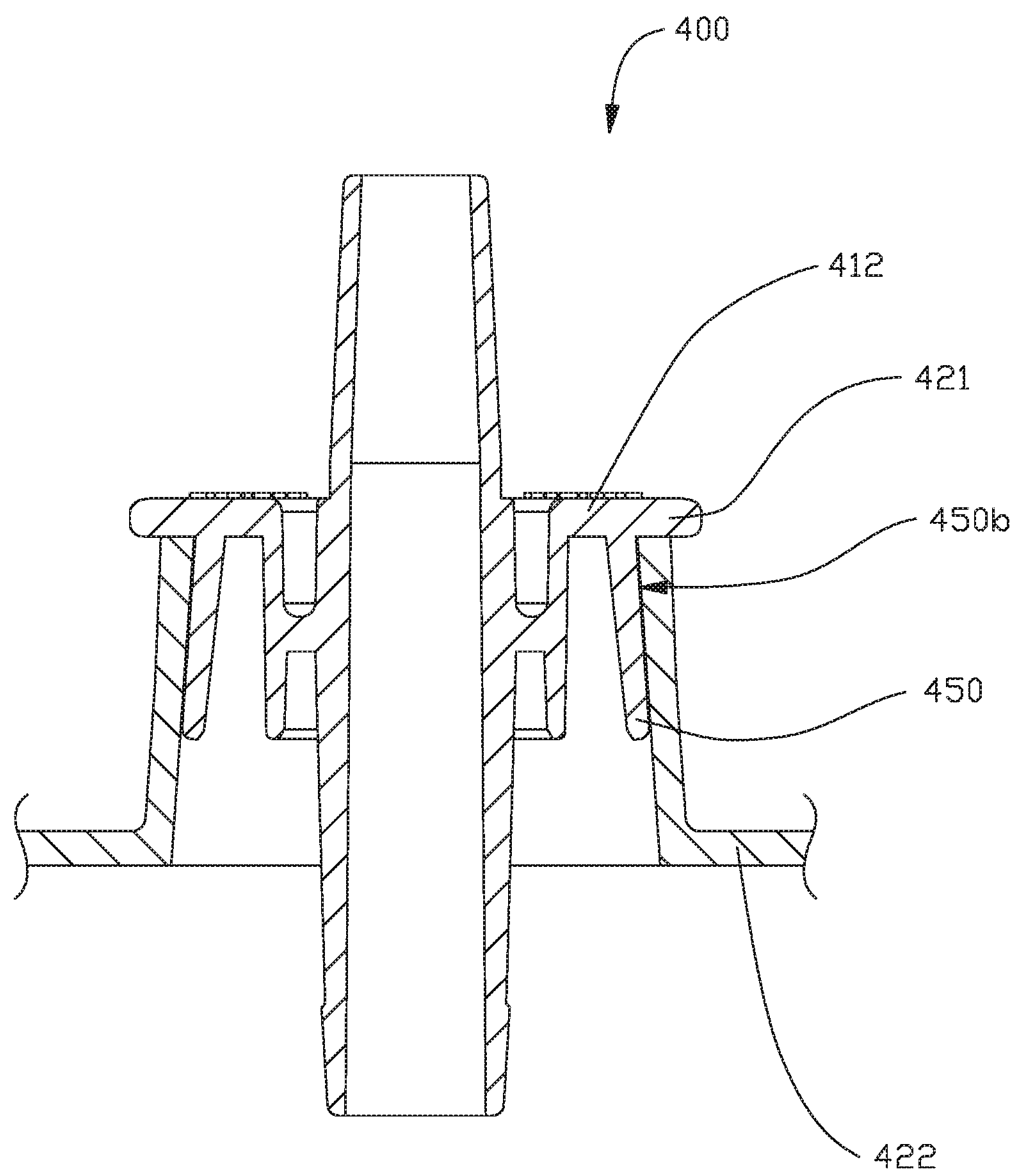
FIG. 7 is a detail section view of a connector in accordance with various other aspects of the present disclosure.

An example of another embodiment of a connector in accordance with the present disclosure is illustrated in FIG. 7. In this embodiment, like the connector 100, the inner skirt wall 442 of connector 400 is configured to mate with the outer surface of a tandem port riser 332, but unlike connector 100, the outer skirt wall 450 of connector 400 is configured to mate with the sampling port 320 such that the outer surface 450*b* of the outer skirt wall 450 engages an inner surface of the sampling port riser 322. In this embodiment, the rim 323 of the sampling port 320 abuts a portion 421 of the outer closure wall 112 that extends radially distal of the outer surface 450*b* of the outer skirt wall 450. It should be noted that, like the outer closure wall of the connector 100, this portion 421 of the outer closure wall 412 may be varied to control the height of the connector 400 relative to the lid 300.

It will be appreciated by those skilled in the art that various features known in the art may be implemented with a variety of configurations without straying beyond the scope of this disclosure. For example, in some variations, a connector in accordance with the present disclosure may be configured such that both the inner and outer skirt walls are configured to engage inner surfaces of two different port risers. In some variations, the main body serves as the inner skirt wall, such that an outer surface of the main body is configured to engage an inner surface of a port riser. In other variations, the connector is configured such that both an outer surface of the main body and an inner surface of an inner skirt wall simultaneously engage opposing inner and outer surfaces of a port cone riser.

In some variations, more than two skirt walls may be provided to accommodate more than two different types of ports. In some alternative configurations, a single skirt wall may be provided such that an inner surface of the skirt wall is configured to engage an outer surface of a port riser having a relatively smaller diameter, and an outer surface of the skirt wall is configured to engage an inner surface of a port riser having a relatively larger diameter. Closure walls or other stop features may be provided at varying heights on either side of each skirt wall to individually control the height of the connector when seated on each port riser. In various embodiments, one or more annular skirt walls may include either internal or external, or both internal and external threads, barbs, ribs, rings, embossments, or any other similar gripping, coupling, sealing or locking features.

In certain aspects, the upper portion of the connector may include a generally cylindrical or conical riser portion for receiving a tube or similar device capable of communicating fluid and/or suction to and from the conduit of the connector. The riser portion may include barbs, ribs, tabs, or other features for improving connection strength between the riser portion and various connected accessories. In certain aspects, the lower body portion may extend downward a greater distance than the skirt walls of the connector, thereby defining a lower opening of the primary conduit that is positioned lower than the annular skirt walls. In various aspects, the lower body portion may include a shoulder, step, ledge, ribs, tabs or other similar feature for gripping or engaging a port to provide secure or locking engagement of the connector with the port. In certain aspects, the outer portion of the connector includes spaced apart radial protrusions, gnarled surfaces, or other similar features to provide a better gripping area for a user to aid in installation and removal of the connector. In various embodiments, the upper portion of the connector may include a bend or turn or branch in order to accommodate one or more tubing connections, including connections that are not co-axial with the central longitudinal axis. For example, the upper portion of the connector may include a right angle bend such that a tube mounted to the connector extends generally horizontal (i.e., parallel to the surface of the lid). As another example, the upper portion of the connector may include a "Y" or "T" branch to accommodate multiple tubing connections to the same connector.

Although portions of the connector disclosed herein, such as the main body and skirt walls, are illustrated and described as being generally cylindrical or otherwise radially symmetric about the longitudinal axis (i.e., having circular cross-sections), various other geometries may be implemented without straying beyond the scope of this disclosure. For example, the main body and/or skirt walls may be conical and/or may vary in wall thickness to accommodate various port configurations and ensure secure connections. Furthermore, the skirt walls, the main body, and/or other features and portions thereof of the connector may, for example, have cross-sections orthogonal to the longitudinal axis that are oval, square, polygonal, asymmetric, etc. Moreover, the central longitudinal axis of the lumen may be offset from or askew to a central longitudinal axis of the main body and/or one or more of the skirt walls.

The foregoing description is provided to enable any person skilled in the art to practice the various example implementations described herein. Various modifications to these variations will be readily apparent to those skilled in the art, and the generic principles defined herein may be applied to other implementations. All structural and functional equivalents to the elements of the various illustrious examples described throughout this disclosure that are known or later come to be known to those of ordinary skill in the art are expressly incorporated herein by reference.

KEY OF REFERENCE CHARACTERS

100 connector
102 main body portion
102*a* inner surface
102*b* outer surface
104 upper body portion
106 middle body portion
108 lower body portion
110 inner closure wall
112 outer closure wall
122 ledge
130 primary conduit
132 primary conduit upper opening
134 primary conduit lower opening
142 inner annular skirt wall
142*a* inner skirt wall inner surface

142*b* inner skirt wall outer surface
142*c* inner skirt wall lower portion
142*d* inner skirt wall lower rim
142*e* inner skirt wall upper portion
150 outer annular skirt wall
150*a* outer skirt wall inner surface
150*b* outer skirt wall outer surface
150*c* outer skirt wall lower rim
200 tandem tube assembly
202 tubing segment
204 fitting
300 lid
301 vacuum port
310 patient port
320 sampling port
322 sampling port riser
323 sampling port rim
325 sampling port lumen
330 tandem port
332 tandem port riser
333 tandem port rim
335 tandem port lumen
338 lower port cone
339 lower rim
400 connector
412 outer closure wall
421 outer closure wall portion
442 inner skirt wall
450 outer skirt wall
450*b* outer skirt wall outer surface

We claim:

1. A medical waste fluid collection system comprising:

a lid provided with a first port and a second different port; and a connector configured to connect with at least two different medical fluid container port configurations, the connector comprising:

a main body extending along a primary axis and defining a lumen, the lumen extending between a lower mouth at a lower portion of the main body and an upper mouth at an upper portion of the main body;

a first mating portion; and a second mating portion;

wherein the first mating portion and the first port are configured to engage each other such that the lower mouth of the connector extends a predetermined distance into an interior of the medical waste fluid collection system when the connector is connected with the first port; and wherein the second mating portion and the second port are configured to engage each other such that the lower mouth of the connector extends the same predetermined distance into the interior of the medical waste fluid collection system when the connector is connected with the second port, the second port being larger than the first port.

2. The system of claim 1, the connector further comprising a ledge configured to restrict translation of the connector in at least one direction along the primary axis when the connector is connected with either or each of the first port and the second port.

3. The system of claim 1, wherein the first mating portion of the connector includes a first mating wall extending in a direction along the primary axis, the first mating wall configured to seal with the first port when the connector is connected with the first port.

4. The system of claim 3, wherein the main body of the connector comprises the first mating wall.

5. The system of claim 3, the connector further comprising a first closure wall extending in a direction transverse to the primary axis and coupling the first mating wall and the main body.

6. The system of claim 3, wherein the second mating portion of the connector includes a second mating wall extending in a direction along the primary axis, the second mating wall configured to seal with the second port when the connector is connected with the second port.

7. The system of claim 6, the connector further comprising a second closure wall extending in a direction transverse to the primary axis and coupling the first mating wall and the second mating wall.

8. The system of claim 6, wherein an outer surface of the first mating wall of the connector seals with the first port when the connector is connected with the first port.

9. The system of claim 8, wherein an outer surface of the second mating wall of the connector seals with the second port when the connector is connected with the second port.

10. The system of claim 8, wherein an inner surface of the second mating wall of the connector seals with the second port when the connector is connected with the second port.

11. The system of claim 6, wherein an inner surface of the first mating wall of the connector seals with the first port when the connector is connected with the first port.

12. The system of claim 11, wherein an outer surface of the second mating wall of the connector seals with the second port when the connector is connected with the second port.

13. The system of claim 11, wherein an inner surface of the second mating wall of the connector seals with the second port when the connector is connected with the second port.

14. The system of claim 3, wherein both an outer surface of the main body of the connector and an inner surface of the second mating wall of the connector seal with the first port when the connector is connected with the first port.

* * * * *